United States Patent
Nasu

(10) Patent No.: US 11,932,598 B2
(45) Date of Patent: Mar. 19, 2024

(54) POLYACYLOXYMETHYL-4,4'-ACYLOXYBIPHENYL COMPOUND

(71) Applicant: HONSHU CHEMICAL INDUSTRY CO., LTD., Tokyo (JP)

(72) Inventor: Akihito Nasu, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 598 days.

(21) Appl. No.: 16/973,398

(22) PCT Filed: Jul. 3, 2019

(86) PCT No.: PCT/JP2019/026532
§ 371 (c)(1),
(2) Date: Dec. 8, 2020

(87) PCT Pub. No.: WO2020/017331
PCT Pub. Date: Jan. 23, 2020

(65) Prior Publication Data
US 2021/0323906 A1    Oct. 21, 2021

(30) Foreign Application Priority Data

Jul. 17, 2018  (JP) .................. 2018-134139

(51) Int. Cl.
*C07C 69/21*    (2006.01)

(52) U.S. Cl.
CPC .................. *C07C 69/21* (2013.01)

(58) Field of Classification Search
CPC .................. C07C 69/21; C08G 59/40
See application file for complete search history.

(56) References Cited

U.S. PATENT DOCUMENTS

| | | | |
|---|---|---|---|
| 4,001,279 A | 1/1977 | Cram | |
| 2009/0118417 A1 | 5/2009 | Tachikawa et al. | |
| 2017/0315268 A1 | 11/2017 | Tanaka et al. | |

FOREIGN PATENT DOCUMENTS

| | | | |
|---|---|---|---|
| CN | 101415748 A | | 4/2009 |
| CN | 102317341 A | | 1/2012 |
| CN | 105723257 A | | 6/2016 |
| GB | 1544417 | * | 4/1979 |
| GB | 1544417 A | | 4/1979 |
| JP | S5257248 A | | 5/1977 |
| JP | 2006096838 A | | 4/2006 |
| JP | 2010241877 A | | 10/2010 |

OTHER PUBLICATIONS

Wessely et al. (Reaction of lead tetraacetate with phenols. VII, Chemische Berichte, vol. 93, pp. 2840-2851, Published 1960. Cited in IDS filed Dec. 8, 2020). (Year: 1960).*
Notification (PCT/IB/326) and Notification (PCT/IB/338) dated Jan. 28, 2021, with International Preliminary Report on Patentability (PCT/IB/373) and Written Opinion of the International Searching Authority (PCT/ISA/237), for corresponding international application PCT/JP2019/026532 (11 pages).
A First Office Action issued by the State Intellectual Property Office of dated Apr. 7, 2023, for Chinese counterpart application No. 201980045765.8 (6 pages).
International Search Report (ISR) dated Sep. 17, 2019, issued for International application No. PCT/JP2019/026532. (2 pages).
Mathai, Mannich reaction on biphenols, Journal of the Indian Chemical Society, 1966, vol. 43, No. 6, pp. 421-424 (4 pages).
Wessely et al., Reaction of lead tetraacetate with phenols. VII, Chemische Berichte, 1960, vol. 93, pp. 2840-2851 (12 pages).

* cited by examiner

*Primary Examiner* — Jafar F Parsa
*Assistant Examiner* — Blaine G Doletski
(74) *Attorney, Agent, or Firm* — Law Office of Katsuhiro Arai

(57) ABSTRACT

The present invention addresses the problem of providing a novel compound which readily dissolves in liquid epoxy resins and which can be a hardener for epoxy resins to give cured objects excellent in terms of heat resistance and chemical resistance. Provided as a means for solving the problem is a polyacyloxymethyl-4,4'-acyloxybiphenyl compound represented by formula (1).

1 Claim, No Drawings

POLYACYLOXYMETHYL-4,4'-ACYLOXYBIPHENYL COMPOUND

TECHNICAL FIELD

The present invention relates to a novel poly acyloxymethyl-4,4'-acyloxybiphenyl compound.

BACKGROUND ART

Epoxy resins have a good balance among various properties, such as moldability, electrical properties, moisture resistance, heat resistance, mechanical properties, and adhesiveness to insert parts, and thus are widely used in many industrial fields of electricity, paint, adhesive, and the like. Since various kinds of hardeners can be used for epoxy resins and the properties of cured objects greatly vary by selection of the hardener, an appropriate hardener is selectively used depending on the use purpose.

As general hardeners for epoxy resins, phenolic hardeners, amide hardeners, imidazole hardeners, active ester hardener, and the like are known, and among them, phenolic hardeners are generally used due to advantages of the low cost and the like as well as the variety. Generally, many phenolic hardeners have solid nature due to the hydrogen bond of the phenolic hydroxy groups, and, in particular, highly crystalline ones are unfortunately hardly miscible with epoxy resin compositions, reducing the flowability of the epoxy resin compositions. As one resolution of this problem, a means of preventing or inhibiting the hydrogen bond by the hydroxy group in the phenolic hardener is used. For example, a phenol derivative in which the phenolic hydroxy groups are partially or completely protected with a silyl group (see PTL 1) and a means of introducing a substituent to the ortho position of the phenolic hydroxy group (see PTL 2) are used. In particular, when an allyl group is introduced to the ortho position of the phenolic hydroxy group, the hydrogen bond of the phenolic hydroxy group is inhibited by the allyl group and the resultant compound is liable to be a liquid state at room temperature. However, in such phenolic hardeners, since the allyl group interferes with the reaction with an epoxy group, there have also been problems in that the curing rate is low and the heat resistance and the like are also insufficient.
PTL 1: JP-A-2006-096838
PTL 2: JP-A-2010-241877

SUMMARY OF INVENTION

Technical Problems

The present invention has been made against a background of the above circumstances, and has an object to provide a novel compound that readily dissolves in liquid epoxy resins and that can be a hardener for epoxy resins to give cured objects excellent in heat resistance and chemical resistance.

Solution to Problems

As a result of an intensive study for solving the above problems, the present inventor has found a novel compound in which a plurality of acyloxymethyl groups are substituted on a 4,4'-acyloxybiphenyl skeleton, completing the present invention.

The present invention is as follows.
1. A polyacyloxymethyl-4,4'-acyloxybiphenyl compound represented by the following formula (1):

[Chem. 1]

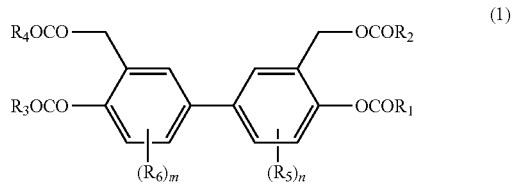

wherein $R_1$, $R_2$, $R_3$, and $R_4$ each independently represent an alkyl group having 1 to 8 carbon atoms; $R_5$ and $R_6$ each independently represent an alkyl group having 1 to 8 carbon atoms or —$CH_2OCOR_7$ ($R_7$ represents an alkyl group having 1 to 8 carbon atoms); and n and m each independently represent any one of 0, 1, 2, and 3.

Advantageous Effects of Invention

Since the polyacyloxymethyl-4,4'-acyloxybiphenyl compound of the present invention has a lower melting point as compared with existing hardeners for epoxy resins having a biphenol skeleton, the compound is miscible with other components at around 140° C. which is a temperature of epoxy resin curing reactions. Accordingly, there is an advantageous effect in that no solvent for dissolving the hardener is needed, or even when a solvent is used, the amount of the solvent used can be largely reduced due to the high solubility in the solvent.

Furthermore, the polyacyloxymethyl-4,4'-acyloxybiphenyl compound of the present invention has many functional groups, which largely contributes to increase in heat resistance and chemical resistance of epoxy resin film. The compound is thus very useful.

In addition, the polyacyloxymethyl-4,4'-acyloxybiphenyl compound of the present invention is also useful as a starting material of a phenolic compound.

DESCRIPTION OF EMBODIMENTS

The present invention will be described in detail below.
The compound of the present invention is a polyacyloxymethyl-4,4'-acyloxybiphenyl compound represented by the following formula (1):

[Chem. 2]

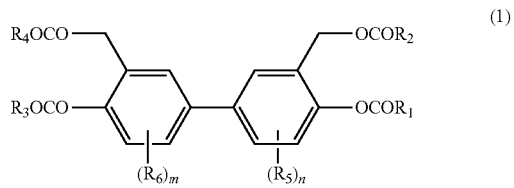

wherein, $R_1$, $R_2$, $R_3$, and $R_4$ each independently represent an alkyl group having 1 to 8 carbon atoms; $R_5$ and $R_6$ each independently represent an alkyl group having 1 to 8 carbon atoms or —$CH_2OCOR_7$ ($R_7$ represents an alkyl group having 1 to 8 carbon atoms); and n and m each independently represent any one of 0, 1, 2, and 3.

In the formula (1), when $R_1$ to $R_6$ or $R_7$ are an alkyl group having 1 to 8 carbon atoms, a linear or branched alkyl group is included. Preferred alkyl groups are linear or branched alkyl groups having 1 to 5 carbon atoms, and specific examples thereof include a methyl group, an ethyl group, a n-propyl group, an i-propyl group, a n-butyl group, an i-butyl group, a t-butyl group, a n-pentyl group, an i-pentyl group, and a t-pentyl group. Among them, any of a methyl group, an ethyl group, and a n-propyl group is preferred. In addition, a substituent can be bonded to the alkyl group to the extent that the effects of the present invention are not impaired, and examples of such a substituent include a phenyl group and an alkoxy group.

When $R_5$ and $R_6$ are an acyloxymethyl group (—$CH_2OCOR_7$), the site of substitution is preferably the ortho position of the acyloxy group.

In addition, in the formula (1), n and m are preferably each independently 1, 2, or 3, and n and m are particularly preferably 1.

As the compound represented by the formula (1), for example, 4,4'-diacetoxy-3,3',5,5'-tetra(acetoxymethyl)biphenyl represented by the following chemical formula is preferred.

[Chem. 3]

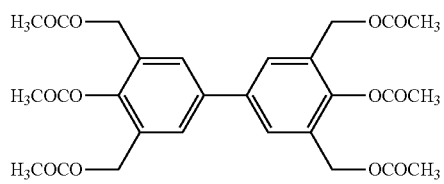

Another preferred example of the compound is 4,4'-diacetoxy-3,3'-di(acetoxymethyl)-5,5'-dimethylbiphenyl represented by the following chemical formula.

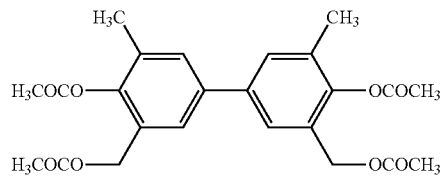

The production method of the polyacyloxymethyl-4,4'-acyloxybiphenyl compound represented by the formula (1) of the present invention is not particularly limited, and the compound can be produced by a known method.

For example, the compound can be produced by a two-step reaction in which a secondary amine compound, such as dimethylamine, and formalin (aqueous formaldehyde solution) are reacted with a biphenol, such as 4,4'-dihydroxybiphenyl, to introduce a di-substituted aminomethyl group into the biphenol (Step 1), and an acid anhydride, such as acetic acid anhydride, is reacted therewith (Step 2).

Starting materials for producing the compound of the present invention are mentioned here. Examples of the biphenol include 4,4'-dihydroxybiphenyl, 3,3'-dimethyl-4,4'-dihydroxybiphenyl, and 2,2',3,3',5,5'-hexamethyl-4,4'-dihydroxybiphenyl. Examples of the secondary amine include dimethylamine, diethylamine, and morpholine, and among them, dimethylamine can be suitably used in terms of the reactivity and handleability. Examples of the acid anhydride include acetic acid anhydride, propionic acid anhydride, butyric acid anhydride, and pivalic acid anhydride.

One example of the above production method is a production method as represented by the following reaction formula in which 4,4'-dihydroxybiphenyl as a starting material, dimethylamine, and acetic acid anhydride are used to obtain the polyacyloxymethyl-4,4'-acyloxybiphenyl compound represented by the formula (1) of the present invention.

[Chem. 4]

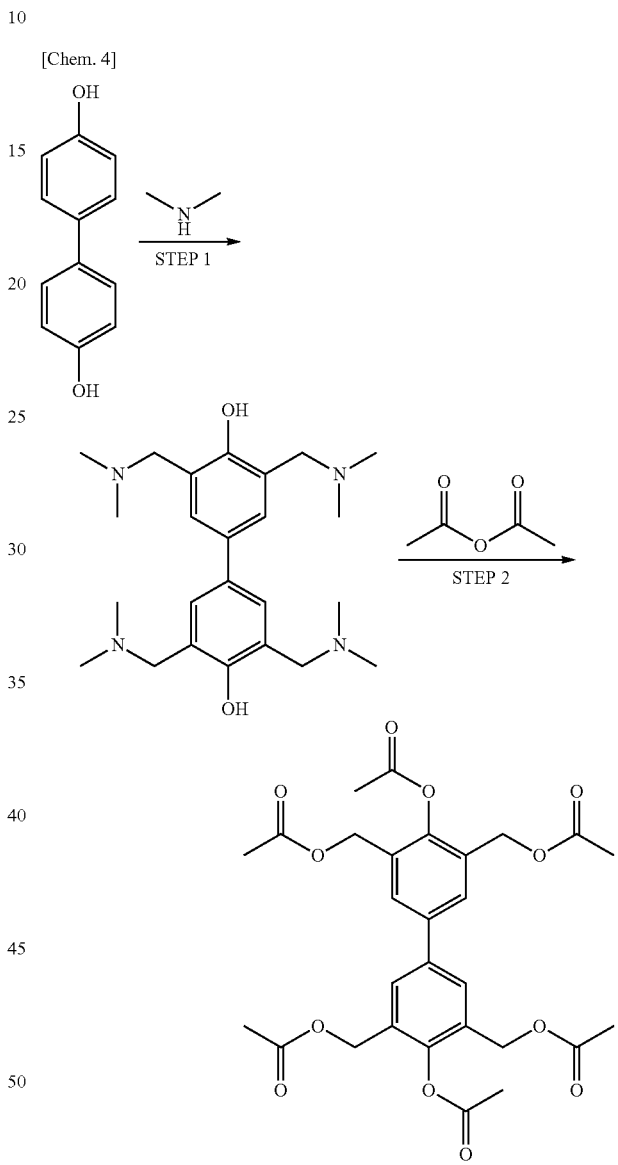

(Step 1)

Regarding the amounts of the secondary amine compound and formalin (aqueous formaldehyde solution) used in Step 1, the amount of the secondary amine compound is 6 to 8 mole times, preferably 6.4 to 7 mole times, and the amount of formaldehyde is 6 to 8 mole times, preferably 6.5 to 7 mole times, per mole of the biphenyl which is a starting material. When the amounts of the secondary amine compound and formaldehyde are each less than 6 mole times per mole of the biphenyl which is a starting material, the reaction hardly proceeds, and when the amounts are each more than 8 mole times, more unreacted materials remain, making the post treatment cumbersome.

The reaction temperature of Step 1 is preferably 60 to 85° C., and more preferably 70 to 80° C. When the reaction temperature is lower than 60° C., the starting material or the product precipitates, for example, thus resulting in impediment of the reaction, and when the temperature is higher than 85° C., it is required to address the odor of the secondary amine compound, which are not preferred. The reaction pressure may be any of normal pressure, an increased pressure, and a reduced pressure, but a reaction under normal pressure is preferred.

For the purpose of increasing the reaction rate, a catalyst may be used as required, and when a catalyst is used, the catalyst is preferably used in an amount of about 1 mole per mole of the secondary amine compound. As a catalyst in Step 1, acetic acid is suitable.

Step 1 is preferably carried out in a solvent. The solvent used is selected from: ether solvents, such as diethyl ether, dipropyl ether, 1,2-dimethoxyethane, diethylene glycol dimethyl ether, tetrahydrofuran, 1,4-dioxane, diisobutyl ether, and diphenyl ether; or alcohol solvents, such as methanol, ethanol, 1-propanol, 2-propanol, 1-butanol, 2-butanol, isobutylalcohol, 2-methyl-2-propanol, cyclohexanol, ethylene glycol, ethylene glycol monomethyl ether, and diethylene glycol; aromatic hydrocarbon solvents, such as benzene, toluene, xylene, ethylbenzene, and mesitylene; ketone solvents, such as acetone, 2-butanone, 3-pentanone, cyclohexanone, and methyl isobutyl ketone; and carboxylic acid solvents, such as acetic acid and propionic acid. These solvents may be mixed. Acetic acid may be used both as a reaction solvent and a catalyst.

After completion of the reaction, a solvent that separates from water, such as toluene, and water are added to the mixture after reaction, which is stirred and allowed to stand, and the aqueous layer is removed. Neutralization may be performed here as required, and furthermore, a water washing operation in which water is added to the resulting organic layer, then stirred and allowed to stand, followed by removal of the aqueous layer may be carried out one or more times. Water is removed from the resulting organic layer with a Dean Stark apparatus or the like to obtain a solution containing a target product, which can be used in the next Step 2.

(Step 2)

The amount of an acid anhydride used in Step 2 is 7.5 to 12 mole times, preferably 8 to 9 mole times per mole of the biphenol which is a starting material of Step 1. When the amount of the acid anhydride used is less than 7.5 mole times, the reaction tends to be slower and byproducts tend to increase, and when the amount is more than 12 mole times, more unreacted materials remain, making the post treatment cumbersome.

The reaction temperature in Step 2 is preferably 100 to 130° C., more preferably 115 to 125° C. When the reaction temperature is lower than 100° C., the starting material or the product precipitates, for example, thus resulting in impediment of the reaction, and when the temperature is higher than 130° C., the target product thermally decomposes, which are not preferred. The reaction pressure may be any of normal pressure, an increased pressure, and a reduced pressure, but a reaction under normal pressure is preferred.

For the purpose of increasing the reaction rate, a catalyst may be used as required, and when a catalyst is used, the catalyst is preferably used in an amount of about 0.1 mole times per mole of the biphenol which is a starting material of Step 1. As a catalyst in Step 2, sodium acetate is suitable.

Step 2 is preferably carried out in a solvent. The aromatic hydrocarbon solvent that separates from water, such as toluene, which is used in the post treatment of the reaction of Step 1, is preferably used continuously as the reaction solvent.

A post treatment method for Step 2 in the above production method will be described below.

The endpoint of the reaction may be given by liquid chromatography or gas chromatography. The time point when the polyacyloxymethyl-4,4'-acyloxybiphenyl compound which is the target product is no longer increased is preferably taken as the endpoint of the reaction.

After completion of the reaction, unreacted acid anhydride is removed, for example, by distillation under reduced pressure, then an organic solvent that separates from water and water are added to the residue, which is then stirred and allowed to stand, and the aqueous layer is removed. Furthermore, a water washing operation in which water is added to the resulting oil layer, then stirred and allowed to stand, followed by removal of the aqueous layer may be carried out one or more times as required. After the solvent is removed from the resulting organic solvent layer by distillation, a solvent is added to the residue of the distillation, which is then heated to dissolve the residue. The solution is cooled, and precipitated crystals are filtered and dried to obtain the target product as high-purity or crude crystals.

The target product obtained as above can be further purified by recrystallization using a solvent. Examples of an organic solvent used here include: aromatic hydrocarbons, such as toluene, xylene, and mesitylene; ketones, such as acetone, methyl ethyl ketone, methyl isobutyl ketone, and cyclohexanone; and esters, such as ethyl acetate and butyl acetate; alcohols, such as methanol, ethanol, and butanol; ethers, such as tetrahydrofuran and dioxolane; and saturated aliphatic hydrocarbons, such as hexane, heptane, and cyclohexane. The solvents may be used alone or in mixture of two or more thereof.

In place of the above crystallization operation, an operation in which the reaction solvent or the like is concentrated under reduced pressure after completion of the reaction and the residue is purified, for example, by column chromatography can be performed to obtain a high-purity product.

Since the polyacyloxymethyl-4,4'-acyloxybiphenyl compound represented by the formula (1) of the present invention obtained by the above production method or the like has a lower melting point as compared with existing hardeners for epoxy resins, the compound is superior in miscibility with other components at a temperature of epoxy curing reactions and thus can be suitably used as a hardener for epoxy resins.

In addition, the polyacyloxymethyl-4,4'-acyloxybiphenyl compound represented by the formula (1) of the present invention, when used as a hardener for epoxy resins, can contribute to increase in the heat resistance and chemical resistance in epoxy resin film due to the chemical structure having many functional groups, and thus the compound is useful.

EXAMPLES

The present invention will be specifically described below with reference to Examples, but the present invention is not to be limited to the Examples.

The reaction endpoint detection and purity measurement in Examples are performed by the following methods.

[Analytical Method]

1. Purity Measurement

Device: LAB Solutions (liquid chromatography), manufactured by Shimadzu Corporation Pump: LC-20AT
Column oven: CTO-20A
Detector: SPD-20A
Column: Shim-pack CLC-ODS, inner diameter 6 mm, length 150 mm
Oven temperature: 50° C.
Flow rate: 1.0 ml/min
Mobile phase: (A) 0.2 vol % aqueous acetic acid solution, (B) methanol
Gradient condition: (B) vol % (time from the start of analysis)
50% (0 min)→100% (30 min)→100% (45 min)
Sample injection: 20 μl
Detection wavelength: 280 nm
2. Melting Point 3.418 mg of crystals were weighed on an aluminum pan, and were analyzed using a differential scanning calorimeter (DSC-60, manufactured by Shimadzu Corporation) with aluminum oxide as a control under the following operation conditions.
(Operation Conditions)
Temperature rising rate: 10° C./min
Measurement temperature range: 30 to 400° C.
Measurement atmosphere: open, nitrogen 50 mL/min
3. NMR Analysis
Apparatus: Ascend TM 400, manufactured by BRUKER Example 1

Production of 4,4'-Diacetoxy-3,3',5,5'-tetra(acetoxymethyl)biphenyl

Into a 3 L four-neck flask equipped with a thermometer, a stirrer, a dropping funnel, and a condenser, 285 g (1.53 mol) of 4,4'-dihydroxybipheny, 285 g of isopropanol, and 880.4 g (10.3 mol) of 35% formalin (aqueous formaldehyde solution) were put, and 883.5 g (9.8 mol) of a 50% aqueous dimethylamine solution was added dropwise while keeping the inner temperature at 30° C. or lower. Subsequently, while keeping the inner temperature at 80 to 85° C., stirring was continued for 2 hours (Step 1).

Then, toluene and water were added to the resulting liquid after reaction, followed by stirring. Then an operation of separating the aqueous layer was performed, and water was distilled from the organic layer through reflux under reduced pressure using a Dean Stark apparatus. To the resulting bottom liquid (purity: 99.0%, by high performance liquid chromatography, area %), 1535.1 g (15.3 mol) of acetic acid anhydride was added over 2 hours while keeping the inner temperature at 78 to 82° C. Subsequently, the temperature was increased to 120° C. and stirring was continued for 2 hours (Step 2).

Then, from the resulting liquid after reaction, unreacted acetic acid anhydride and the like were removed by distillation under reduced pressure, then toluene and water were added, followed by stirring. Then, after an operation of separating the aqueous layer, toluene was removed by distillation under reduced pressure. Subsequently, 178.5 g of methanol was added at an inner temperature in the range of 40 to 50° C., and precipitated crystals were filtered to obtain 598.2 g of 4,4'-diacetoxy-3,3',5,5'-tetra(acetoxymethyl)biphenyl.

Purity: 98.9% (high performance liquid chromatography, area %)
Yield: 70% (based on the starting 4,4'-dihydroxybiphenyl)

Melting point: 116.2° C. (differential scanning calorimeter)
Proton nuclear magnetic resonance spectrum (400 MHz, solvent $CDCl_3$, standard TMS): 2.1 ppm (s, 6H), 2.4 ppm (s, 12H), 5.1 ppm (s, 8H), 7.6 ppm (s, 4H).
Carbon 13 nuclear magnetic resonance spectrum (400 MHz, solvent $CDCl_3$, standard TMS): 20.4 ppm, 20.7 ppm, 61.2 ppm, 129.4 ppm, 129.7 ppm, 138.2 ppm, 147.4 ppm, 169.1 ppm, 170.4 ppm.

The melting point of 4,4'-diacetoxy-3,3',5,5'-tetra(acetoxymethyl)biphenyl obtained in Example 1 was 116.2° C. as described above. In contrast, the melting point of 4,4'-di(acetoxy)biphenyl which is used as a hardener for epoxy resins is 163° C.

In other words, it became clear that the polyacyloxymethyl-4,4'-acyloxybiphenyl compound represented by the formula (1) of the present invention is characterized by a largely decreased melting point due to the chemical structure having a plurality of acyloxymethyl groups.

Next, the solvent solubility of the polyacyloxymethyl-4,4'-acyloxybiphenyl compound represented by the formula (1) of the present invention will be examined.
<Solvent Solubility Evaluation Test>

The 4,4'-Diacetoxy-3,3',5,5'-tetra(acetoxymethyl)biphenyl obtained in Example 1 (hereinafter referred to as "Present Compound A") and 4,4'-di(acetoxy)biphenyl (hereinafter referred to as "Comparative Compound a") were measured for the amounts dissolved in 100 g of cyclohexanone at 40° C. and 60° C. (hereinunder referred to as "solubility (g)"). The results are shown together in Table 1.

TABLE 1

| | | Present Compound A | Comparative Compound a |
|---|---|---|---|
| Solubility (g) | 40° C. | 39.4 | 9.0 |
| | 60° C. | 89.8 | 12.8 |

It became clear from the results in Table 1 that the polyacyloxymethyl-4,4'-acyloxybiphenyl compound represented by the formula (1) of the present invention has a largely increased solubility in a solvent due to the chemical structure having a plurality of acyloxymethyl groups.

Since the polyacyloxymethyl-4,4'-acyloxybiphenyl compound represented by the formula (1) of the present invention has a lower melting point as compared with existing hardeners for epoxy resins having a biphenol skeleton, the compound can be miscible with other components at around 140° C. which is a temperature of epoxy resin curing reactions, and thus no solvent for dissolving the hardener is needed. In addition, since the compound has high solubility in a solvent, even when a solvent is used, the amount of the solvent used can be largely reduced. Accordingly, the compound is very useful.

The invention claimed is:
1. A polyacyloxymethyl-4,4'-acyloxybiphenyl compound represented by a following formula (1):

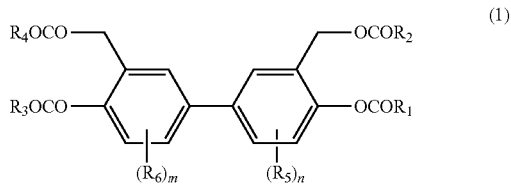

wherein, $R_1$, $R_2$, $R_3$, and $R_4$ each independently represent an alkyl group having 1 to 8 carbon atoms; $R_5$ and $R_6$ each independently represent —$CH_2OCOR_7$, $R_7$ represents an alkyl group having 1 to 8 carbon atoms; and n and m each independently represent any one of 1, 2, and 3.

* * * * *